(12) United States Patent
Le Hen-Ferrenbach

(10) Patent No.: US 6,313,085 B1
(45) Date of Patent: Nov. 6, 2001

(54) HIGH-CONCENTRATION FLOWABLE ANIONIC SURFACTANT MIXTURES CONTAINING ALKYL ETHER SULFATES AND ALKYL SULFATES

(75) Inventor: Catherine Le Hen-Ferrenbach, Meaux (FR)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/606,596

(22) Filed: Jun. 29, 2000

(30) Foreign Application Priority Data

Jun. 29, 1999 (DE) .............................................. 199 29 511

(51) Int. Cl.⁷ .................................................... C11D 17/00
(52) U.S. Cl. .......................... 510/428; 510/424; 510/426; 510/428
(58) Field of Search .................................. 510/424, 426, 510/428

(56) References Cited

U.S. PATENT DOCUMENTS

| | | |
|---|---|---|
| 4,172,887 | 10/1979 | Vanlerberghe et al. . |
| 4,544,493 | * 10/1985 | Silvis ................................... 252/89.1 |
| 5,705,169 | 1/1998 | Stein et al. . |
| 5,730,960 | 3/1998 | Stein et al. . |
| 5,945,091 | 8/1999 | Habeck et al. . |
| 6,087,320 | * 7/2000 | Urfer et al. .......................... 510/470 |

FOREIGN PATENT DOCUMENTS

| | | |
|---|---|---|
| 1 165 574 | 8/1960 | (DE) . |
| 20 24 051 | 12/1971 | (DE) . |
| 197 12 033 | 9/1998 | (DE) . |
| 0 693 471 | 1/1996 | (EP) . |
| 0 694 521 | 1/1996 | (EP) . |
| 0 818 450 | 1/1998 | (EP) . |
| 2 252 840 | 6/1995 | (FR) . |
| 962 919 | 7/1964 | (GB) . |
| 1 333 475 | 10/1973 | (GB) . |

OTHER PUBLICATIONS

Surfactants in Consumer Products, Springer Verlag, (1987) pp. 61–63 *NMA.
C.Todd, Volatile silicone fluids for cosmetic formulations, Cosmetics & Toiletries, vol. 91, (1976) pp.29–32 *NMA.
R. Lochhead, W. Fron, *Encyclopedia of Polymers and Thickeners*, Cosmetics & Toiletries, vol. 108, (1993) pp. 95–135 * NMA.
P. Finkel, Formulierung kosmetischer Sonnenschutzmittel, SOEFW–Journal, 122, pp. 543–548 (1996).
Kosmetische Faerbemittel (1984) pp. 81–106 *NMA.

* cited by examiner

*Primary Examiner*—Necholus Ogden
(74) *Attorney, Agent, or Firm*—John E. Drach; Steven J. Trzaska

(57) ABSTRACT

A high-concentrate flowable liquid anionic surfactant composition containing: (a) from 60 to 90% by weight of an alkyl ether sulfate corresponding to formula I:

$$R^1O(CH_2CH_2O)_nSO_3X \qquad (I)$$

wherein $R^1$ is a linear or branched alkyl radical having from 12 to 22 carbon atoms, n is a number having a value of from 1 to 10, and X is an alkali metal, alkaline earth metal, ammonium, alkylammonium, alkanolammonium or glucammonium; and (b) from 10 to 40% by weight of an alkyl sulfate corresponding to formula II:

$$R^2OSO_3X \qquad (II)$$

wherein $R^2$ is a linear or branched alkyl radical having from 12 to 22 carbon atoms, and X is an alkali metal, alkaline earth metal, ammonium, alkylammonium, alkanolammonium or glucammonium, all weights being based on the total weight of the composition, and wherein the composition has a solids content of from 50 to 80% by weight.

18 Claims, No Drawings

HIGH-CONCENTRATION FLOWABLE ANIONIC SURFACTANT MIXTURES CONTAINING ALKYL ETHER SULFATES AND ALKYL SULFATES

BACKGROUND OF THE INVENTION

The invention is in the field of cosmetics and relates to novel anionic surfactant concentrates having defined amounts of alkyl ether sulfates and alkyl sulfates, to a method for the preparation thereof, and to the use thereof in cosmetics.

Alkyl ether sulfates are notable for excellent foaming properties. As well as a high base foam, advantageous foam kinetics are also found, i.e. even in the presence of fats and water hardness a creamy foam is obtained which persists for a long period and does not collapse. Since alkyl ether sulfates are also extremely well tolerated by the skin and have good cleansing properties, they are often used for the preparation of hair and skin cleansing compositions, such as, for example, hair shampoos, shower preparations and the like. A disadvantage, however, is that alkyl ether sulfates do not favor the incorporation of some oily substances, in particular of silicone oils. The formulations are often cloudy and undergo separation, particularly under thermal stress, meaning that further, generally nonionic, emulsifiers have to be co-used. In addition to these application problems, alkyl ether sulfates have the disadvantage that, in high-concentration form, they are virtually cut-resistant pastes which become pumpable only as a result of dilution or warming, which hinders handling.

Accordingly, the object of the present invention was; firstly to provide additives for alkyl ether sulfates so that the miktures are flowable, pumpable and sprayable even in high-concentration form, without the need for the co-use of polyols and consequently without adversely affecting the application properties. Quite the opposite, these novel mixtures should allow the stable incorporation of silicone oils into shampoo formulations.

DESCRIPTION OF THE INVENTION

The invention provides high-concentration flowable aqueous anionic surfactant mixtures having a solids content in the range from 50 to 80% by weight, comprising—based on the surfactant content (a) 60 to 90% by weight of alkyl ether sulfates of the formula (I),

$$R^1O(CH_2CH_2O)_nSO_3X^1 \quad (I)$$

in which $R^1$ is a linear or branched alkyl radical having 12 to 22 carbon atoms, n is a number from 1 to 10, and $X^1$ is alkali metal, alkaline earth metal, ammonium, alkylammonium, alkanolammonium or glucammonium, and (b) 10 to 40% of weight of alkyl sulfates of the formula (II),

$$R^2OSO_3X^2 \quad (II)$$

in which $R^2$ is a linear or branched alkyl radical having 12 to 22 carbon atoms, and $X^2$ is alkali metal, alkaline earth metal, ammonium, alkylammonium, alkanolammonium or glucammonium, with the proviso, that the amounts, optionally with further surfactants, total 100% by weight.

Surprisingly, we have found that the anionic surfactant mixtures according to the invention, despite the high solids content and also without the co-use of polyols, display a viscosity minimum within the given composition as a result of mixed micelle formation, making the compositions flowable, pumpable and, in particular, also sprayable at ambient temperature. The invention encompasses the knowledge that the preparations in particular also permit the stable and nonturbid incorporation of silicone oils which are otherwise difficult to formulate into shampoos, without the foaming and cleansing ability, and the skin cosmetic compatibility being adversely affected.

Anionic Surfactant Mixtures

In a preferred embodiment, the anionic surfactant mixtures have a solids content in the range from 65 to 75% by weight and in particular 70 to 72% by weight, preferably comprising—in each case based on the surfactant content –75 to 85% by weight of alkyl ether sulfates and 15 to 25% by weight of alkyl sulfates. Typical examples of suitable alkyl ether sulfates are sulfates based on the addition products of, on average, 1 to 10 mol of ethylene oxide to lauryl alcohol, isotridecyl alcohol, myristyl alcohol, cetyl alcohol, stearyl alcohol, isostearyl alcohol, arachidyl alcohol and behenyl alcohol, and the technical-grade mixtures thereof, such as, for example, cocoa alcohol, palm alcohol, palm kernel alcohol or tallow alcohol in the form of their sodium, magnesium and/or alkanolamine salts. The mixtures preferably comprise alkyl ether sulfates of the formula (I), in which $R^1$ is an alkyl radical having 12 to 18 carbon atoms and n is a number from 2 to 5. Typical examples of suitable alkyl sulfates are the sulfates of the abovementioned alcohols, likewise again in the form of their sodium, magnesium and/or alkanolamine salts. The mixtures here preferably comprise alkyl sulfates of the formula (II) in which $R^2$ is an alkyl radical having 16 to 18 carbon atoms (cetearyl alcohol sulfate). For the person skilled in the art, the term "high-concentration flowable" means a Brookfield viscosity, measured in an RVT viscometer at a temperature of 20° C., a shear rate of 10 rpm and with a spindle of type 1, of less than 50,000 mPas, preferably less than 30,000 and in particular less than 10,000 mPas.

Preparation Method

In principle, the surfactant mixtures according to the invention can be prepared by mixing the individual substances. However, it preferably takes place by cosulfation of the alcohols. The invention therefore further provides a method for the preparation of anionic surfactant mixtures, in which method mixtures of (a) 60 to 90% by weight of alcohol polyglycol ethers of the formula (III),

$$R^3O(CH_2CH_2O)_nH \quad (III)$$

in which $R^3$ is a linear or branched alkyl radical having 12 to 22 carbon atoms, and n is a number from 1 to 10, and (b) 10 to 40% by weight of alcohols of the formula (IV),

$$R^4OH \quad (IV)$$

in which $R^4$ is a linear or branched alkyl radical having 12 to 22 carbon atoms, are jointly sulfated and neutralized, and in the course of the process the solids content is adjusted to a value in the range from 50 to 80% by weight. The formulae (III) and (IV) correspond here to the formulae (I) and (II), making it unnecessary to again discuss the examples of suitable feed material. The reaction of the starting materials with gaseous sulfur trioxide can be carried out in the manner known for fatty acid lower alkyl esters [J. Falbe (ed.), "Surfactants in consumer products"; Springer Verlag, Berlin-Heidelberg, 1987, p. 61], reactors which operate according to the falling-film principle being preferred. In the process, the sulfur trioxide is diluted with an inert gas, preferably air or nitrogen, and used in the form of a gas mixture which comprises the sulfonating agent in a concentration of from 1 to 8% by volume, in particular 2 to 5% by volume. The molar feed ratio of starting mixture to sulfur trioxide is 1:0.95 to 1:1.8, but preferably 1:1.0 to 1:1.6 and in particular 1:1.3 to 1:1.5. As well as using gaseous sulfur trioxide, another suitable sulfonating agent is chlorosulfonic acid. The joint sulfation is carried out at temperatures of from 15 to 50° C., preferably 25 to 40° C. The sulfuric monoesters which form during the reaction are stirred into aqueous bases, neutralized and adjusted to a pH of from 7.5 to 8.5. Neutralization is carried out using bases chosen from the group formed from alkali metal hydroxides, such as sodium, potassium and lithium hydroxide, alkaline earth metal oxides and hydroxides, such as magnesium oxide, magnesium hydroxide, calcium oxide and calcium hydroxide, ammonia, mono-, di- and tri-$C_{2-4}$-alkanolamines, for example mono-, di- and triethanolamine, and primary, secondary or tertiary $C_{1-4}$-alkylamines. The neutralization bases are preferably used here in the form of 35 to 55% strength by weight aqueous solution. The sulfates obtainable by the method according to the invention are, following neutralization, in the form of aqueous solutions having an active substance content of from 50 to 80% by weight, preferably 65 to 75% by weight. The sulfation products can, following neutralization, be bleached in a manner known per se by adding hydrogen peroxide or sodium hypochlorite solution in order to achieve further color lightening desired for. many applications. For this, based on the solids content in the solution of the sulfation products, 0.2 to 2% by weight of hydrogen peroxide, calculated as 100% strength by weight substance, or corresponding amounts of sodium hypochlorite are used. The pH of the solutions can be kept constant using suitable buffering agents, e.g. using sodium phosphate or citric acid. For stabilization against bacterial attack, preservation is also advisable, e.g. using formaldehyde solution, p-hydroxybenzoate, sorbic acid or other known preservatives.

INDUSTRIAL APPLICABILITY

The anionic surfactant mixtures according to the invention are notable for particular foaming and cleansing properties. They are skin-cosmetically compatible and permit, in particular, the stable incorporation of silicone oils into shampoos. The invention therefore further provides for their use for the preparation of cosmetic preparations in which they can be present in amounts of from 0.1 to 50% by weight, preferably from 1 to 25% by weight and in particular 5 to 15% by weight—based on the compositions.

Cosmetic and/or Pharmaceutical Preparations

The anionic surfactant mixtures according to the invention can be used for the preparation of cosmetic and/or pharmaceutical preparations, such as, for example, hair shampoos, hair lotions, foam baths, shower preparations, decorative cosmetics, creams, gels, lotions, alcoholic and hydro/alcoholic solutions, emulsions, wax/fatty compositions, stick preparations, powders or ointments. As further auxiliaries and additives, these compositions can also comprise mild surfactants, oily substances, emulsifiers, superfatting agents, pearlescent waxes, bodying agents, thickeners, polymers, silicone compounds, fats, waxes, lecithins, phospholipids, stabilizers, biogenic active ingredients, deodorants, antiperspirants, antidandruff agents, film formers, swelling agents, UV light protection factors, antioxidants, hydrotropic agents, preservatives, insect repellents, self-tanning agents, tyrosine inhibitors (depigmentation agents), solubilizers, perfume oils, dyes and the like.

Typical examples of suitable mild, i.e. particularly skin-compatible, surfactants are monoglyceride sulfates, mono- and/or dialkyl sulfosuccinates, fatty acid isethionates, fatty acid sarcosinates, fatty acid taurides, fatty acid glutamates, α-olefinsulfonates, ether carboxylic acids, alkyl oligoglucosides, fatty acid glucamides, alkylaminobetaines and/or protein-fatty acid condensates, the latter preferably being based on wheat proteins.

Suitable oily substances are, for example, Guerbet alcohols based on fatty alcohols having 6 to 18, preferably 8 to 10, carbon atoms, esters of linear $C_6$–$C_{22}$-fatty acids with linear $C_6$–$C_{22}$-fatty alcohols, esters of branched $C_6$–$C_{13}$-carboxylic acids with linear $C_6$–$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl. isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isogtearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$–$C_{22}$-fatty acids with branched alcohols, in particular 2-ethylhexanol, esters of hydroxycarboxylic acids with linear or branched $C_6$–$C_{22}$-fatty alcohols, in particular dioctyl malates, esters of linear and/or branched fatty acids with polyhydric alcohols (such as, for example, propylene glycol, dimerdiol or trimertriol) and/or Guerbet alcohols, triglycerides based on $C_6$–$C_{10}$-fatty acids, liquid mono-/di-/triglyceride mixtures based on $C_6$–$C_{18}$-fatty acids, esters of $C_6$–$C_{22}$-fatty alcohols and/or Guerbet alcohols with aromatic carboxylic acids, in particular benzoic acid, esters of $C_2$–$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$–$C_{22}$-fatty alcohol carbonates, Guerbet carbonates, esters of benzoic acid with linear and/or branched $C_6$–$C_{22}$-alcohols (e.g. Finsolv® TN), linear or branched, symmetrical or unsymmetrical dialkyl ethers having 6 to 22 carbon atoms per alkyl group, ring-opening products of epoxidized fatty acid esters with polyols, silicone oils and/or aliphatic or naphthenic hydrocarbons, such as, for example squalane, squalene or dialkylcyclohexanes.

Suitable emulsifiers are, for example, nonionogenic surfactants from at least one of the following groups:

addition products of from 2 to 30 mol of ethylene oxide and/or 0 to 5 mol of propylene oxide to linear fatty alcohols having 8 to 22 carbon atoms, to fatty acids having 12 to 22 carbon atoms, to alkylphenols having 8 to 15 carbon atoms in the alkyl group, and alkylamines having 8 to 22 carbon atoms in the alkyl radical;

alkyl and/or alkenyl oligoglycosides having 8 to 22 carbon atoms in the alk(en)yl radical and the ethoxylated analogs thereof;

addition products of from 1 to 15 mol of ethylene oxide to castor oil and/or hydrogenated castor oil;

addition products of from 15 to 60 mol of ethylene oxide to castor oil and/or hydrogenated castor oil;

partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mol of ethylene oxide;

partial esters of polyglycerol (average degree of self-condensation 2 to 8), polyethylene glycol (molecular weight 400 to 5000), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mol of ethylene oxide;

mixed esters of pentaerythritol, fatty acids, citric acid and fatty alcohol as in German Patent 1165574 and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof;

wool wax alcohols;

polysiloxane-polyalkyl-polyether copolymers and corresponding derivatives;

polyalkylene glycols, and glycerol carbonate.

The addition products of ethylene oxide and/or of propylene oxide to fatty alcohols, fatty acids, alkylphenols or to castor oil are known, commercially available productS. These are homolog mixtures whose average degree of alkoxylation corresponds to the ratio of the amounts of substance of ethylene oxide and/or propylene oxide and substrate with which the addition reaction is carried out. $C_{12/18}$-fatty acid mono- and diesters of addition products of ethylene oxide to glycerol are known from German Patent 2024051 as refatting agents for cosmetic preparations.

Alkyl and/or alkenyl oligoglycosides, their preparation and their use are known from the prior art. They are prepared, in particular, by reacting glucose or oligosaccharides with primary alcoholos having 8 to 18 carbon atoms. With regard to the glycoside radical, both monoglycosides, in which a cyclic sugar radical is glycosidically bonded to the fatty alcohol, and also oligomeric glycosides having a degree of oligomerization of up to, preferably, about 8, are suitable. The degree of oligomerization here is a statistical average value which is based on a homolog distribution customary for such technical-grade products.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, eruici acid Monoglyceride, erucic acid diglyceride, tartaric acid monoglyceride, tartaric acid diglyceride, citric acid monoglyceride, citric acid diglyceride, malic acid monoglyceride, malic acid diglyceride, and the technical-grade mixtures thereof which may also comprise small amounts of triglyceride as a minor product of the preparation process. Likewise suitable are addition products of 1 to 30 mol, preferably 5 to 10 mol, of ethylene oxide to said partial glycerides.

Suitable sorbitan esters! are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbinate monoerucate, sorbitan sesquierucate, sorbitan dierucate, sorbitan trierucate, sorbitan monoricinoleate, sorbitan sesquiricinoleate, gorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Likewise suitable are addition products of from 1 to 30 mol, preferably 5 to 10 mol, of ethylene oxide to said sorbitan esters.

Typical examples of suitable polyglycerol esters are polyglyceryl-2 dipolyhydroxystearate (Dehymuls® PGPH), polyglycerol-3 diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose disterate (Tego Care® 450), polyglyceryl-3 beeswax (Cera Bellina®), polyglyceryl-4 caprate (Polyglycerol Caprate T2010/90), polyglyceryl-3 cetyl ether (Chimexane® NL), polyglyceryl-3 distearate (Cremophor GS 32) and polyglyceryl polyricinoleate (Admul® WOL 1403), polyglyceryl dimerate isostearate, and mixtures thereof.

Examples of further suitable polyol esters are the mono-, di- and triesters, optionally reacted with 1 to 30 mol of ethylene oxide, of trimethylolpropane or pentaerythritol with lauric acid, coconut fatty acid, tallow fatty acid, palmitic acid, stearic acid, oleic acid, behenic acid and the like.

Furthermore, zwitterionic surfactants can be used as emulsifier. The term zwitterionic surfactants refers to those surface-active compounds which carry at least one quaternary ammonium group and at least one carboxylate and one sulfonate group in the molecule. Particularly suitable zwitterionic surfactants are the so-called betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethylcarboxymethyl glycinate. Particular preference is given to the fatty acid amide derivative known under the CTFA name Cocamidopropyl Betaine. Likewise suitable emulsifiers are ampholytic surfactants. The term ampholytic surfactants means those surface-active compounds which, apart from a $C_{8/18}$-alkyl or -acyl group in the molecule, contain at least one free amino group and at least one —COOH or —SO$_3$H group and are capable of forming internal salts. Examples of suitable ampholytic surfactants are N-alkylglycines, N-alkylaminopropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocoacylaminoethylaminopropionate and $C_{12/18}$-acylsarcosine.

Finally, cationic surfactant are also suitable emulsifiers, those of the ester quat type, preferably methyl-quaternized difatty acid triethanolamine ester salts, being particularly preferred.

Superfatting agents which can be used are substances such as, for example, lanolin and lecithin, and polyethoxylated or acylated lanolin and lecithin derivatives, polyol fatty acid esters, monoglycerides and fatty acid alkanolamides, the latter also serving as foam stabilizers.

Examples of suitable pearlescent waxes are: alkylene glycol esters, specifically ethylene glycol distearate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates, which have a total of at least 24 carbon atoms, specifically laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Suitable bodying agents are primarily fatty alcohols or hydroxy fatty alcohols having 12 to 22, and preferably 16 to 18, carbon atoms, and also partial glycerides, fatty acids or hydroxy fatty acids. Preference is given, to a combination of these substances with alkyl oligoglucosides and/or fatty acid N-methylglucamides of identical chain length and/or polyglycerol poly-12-hydroxystearates.

Suitable thickeners are, for example, Aerosil grades (hydrophilic silicas), polysaccharides, in particular xanthan gum, guar guar, agar agar, alginates and Tyloses, carboxymethylcellulose and hydroxyethyl-cellulose, and also relatively high molecular weight polyethylene glycol mono- and diesters of fatty acids, polyacrylates (e.g. Carbopols® from Goodrich or synthalens® from Sigma), polyacrylamides, polyvinyl alcohol and polyvinylpyrrolidone, surfactants, such as, for example, ethoxylated fatty acid glycerides, esters of fatty acids with polyols such as, for example, pentaerythritol or trimethylolpropane, fatty alcohol ethoxylates having a narrowed homolog distribution or alkyl oligoglucosides, and electrolytes such as sodium chloride and ammonium chloride.

Suitable cationic polymers are, for example, cationic cellulose derivatives, such as, for example, a quaternized hydroxyethylcellulose obtainable under the name Polymer JR 400® from Amerchol, cationic starch, copolymers of diallylammonium salts and acrylamides, quaternized vinylpyrrolidone-vin,limidazole polymers, such as, for example, Luviquat® (BASF), condensation products of polyglycols and amines, quaternized collagen polypeptides, such as, for example, lauryldimonium hydroxypropyl hydrolyzed collagen (Lamequat® L/-Grünau), quaternized wheat polypeptides, polyethyleneimine, cationic silicone polymers, such as, for example, amidomethicones, copolymers of adipic acid and dimethylaminohydroxypropyldiethylenetriamine (Cartaretins®/Sandoz), copolymers of acrylic acid with dimethyldiallylammonium chloride (Merquat® 550/Chemviron), polyaminopolyamides, as described, for example, in FR 2252840 A, and crosslinked water-soluble polymers thereof, cationic chitin derivatives, such as, for example, quaternized chitosan, optionally in microcrystalline dispersion, condensation products from dihaloalkyls, such as, for example, dibromobutane with bisdialkylamines, such as, for example, bisdimethylamino-1,3-propane, cationic guar gum, such as, for example, Jaguar® CBS, Jaguar® C-17, Jaguar® C-16 from Celanese, quaternized ammonium salt polymers, such as, for example, Mirapol® A-15, Mirapol® AD-1, Mirapol® AZ-1 from Miranol.

Suitable anionic, zwitterionic, amphoteric and nonionic polymers are, for example, vinyl acetate-crotonic acid copolymers, vinylpyrrolidone-Yinyl acrylate copolymers, vinyl acetate-butyl maleate-isobornyl acrylate copolymers, methyl vinyl ether-maleic anhydride copolymers and esters thereof, uncrosslinked polyacrylic acids, polyacrylic acids crosslinked with polyols, acrylamidopropyltrimethylammonium chloride-acrylate copolymers, octylacrylamide-methyl methacrylate-tert-butylamino-ethyl methacrylate-2-hydroxypropyl methacrylate copolymers, polyvinylpyrrolidone, vinylpyrrolidone-vinyl acetate copolymers, vinylpyrrolidone-dimethylaminoethyl methacrylate-vinylcaprolactam terpolymers, and optionally derivatized cellulose ethers and silicones.

Suitable silicone compounds are, for example, dimethylpolysiloxanes, methylphenylpolysiloxanes, cyclic silicones, and amino-, fatty-acid-, alcohol-, polyether-, epoxy-, fluorine-, glycoside- and/or alkyl-modified silicone compounds, which can either be liquid or in resin form at room temperature. Also suitable are simethicones, which are mixtures of dimethicones having an average chain length of from 200 to 300 dimethyl-siloxane units and hydrogenated silicates. A detailed review of suitable volatile silicones can additionally be found in Todd et al., Cosm. Toil. 91, 27 (1976).

Typical examples of fate are glycerides, and suitable waxes are inter alia natural waxes, such as, for example, candelilla wax, carnauba wax, japan wax, esparto grass wax, cork wax, guaruma wax, rice germ oil wax, sugarcane wax, ouricury wax, montan wax, beeswax, shellac wax, spermaceti, lanolin (wool wax), uropygial grease, ceresin, ozokerite (earth wax), petrolatum, paraffin waxes, microcrystalline waxes; chemically modified waxes (hard waxes), such as, for example, montan ester waxes, sasol waxes, hydrogenated jojoba waxes, and synthetic waxes, such as, for example, polyalkylene waxes and polyethylene glycol waxes. In addition to the fats, suitable additives are also fat-like substances, such as lecithin and phospholipids. For the person skilled in the art, the term "lecithins" means those glycerophospholipids formed from fatty acids, glycerol, phosphoric acid and choline by esterification. In the specialist field, lecithins are therefore also often referred to as phosphatidylcholines (PC) and follow the general formula

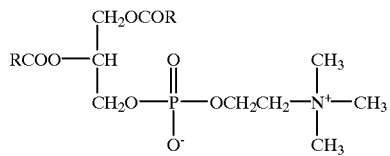

where R is typically a linear aliphatic hydrocarbon radical having 15 to 17 carbon atoms and up to 4 cis double bonds. Examples of natural lecithins which may be mentioned are cephalins, which are also referred to as phosphatidic acids and are derivatives of 1,2-diacyl-sn-glycerol-3-phosphoric acids. By contrast, the term "phospholipids" usually means mono- and, preferably, diesters of phosphoric acid with glycerol (glycerol phosphates) which are generally considered to be fats. In addition, sphingosines and sphingolipids are also suitable.

Stabilizers which can be used are metal salts of fatty acids, such as, for example, magnesium, aluminum and/or zinc stearate or riecinoleate.

The term "biogenic active ingredients" means, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Cosmetic deodorants counteract, mask or remove body odors. Body odors arise as a result of the effect of skin bacteria on apocrine perspiration, with the formation of degradation products which have an unpleasant odor. Accordingly, deodorants comprise active ingredients which act as antimicrobial agents, enzyme inhibitors, odor absorbers or odor masking agents.

Suitable antimicrobial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxydiphenyl ether (triclosan), 4-chloro-3,5-dimethylphenol, 2,2'-methylenebis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monolaurate (GML), diglycerol monocaprate (DMC), salicylic acid N-alkylamides, such as, for example, N-octylsalicylamide or N-decylsalicylamide.

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen® CAT, Henkel KGaA, Düsseldorf/FRG). The substances inhibit enzyme activity, thereby reducing the formation of odor. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Suitable odor absorbers are substances which are able to absorb and largely retain odor-forming compounds. They lower the partial pressure of the individual components, thus also reducing their rate of diffusion. It is important that in this process perfumes must remain unimpaired. Odor absorbers are not effective against bacteria. They comprise, for example, as main constituent, a complex zinc salt of ricinoleic acid or specific, largely odor-neutral fragrances which are known to the person skilled in the art as "fixatives", such as, for example, extracts of labdanum or styrax or certain abietic acid derivatives. The odor masking agents are fragrances or perfume oils, which, in addition to their function as odor masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal raw materials, such as, for example, civet and castoreum. Typical synthetic fragrance compounds are products of the ester, ether, aldehyde, ketone, alcohol and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethol, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniper berry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Antiperspirants reduce the formation of perspiration by influencing the activity of the eccrine sweat glands, thus counteracting underarm wetness and body odor, Aqueous or anhydrous formulations of antiperspirants typically comprise the following ingredients:

astringent active ingredients, oil components, nonionic emulsifiers, coemulsifiers, bodying agents, auxiliaries, such as, for example, thickeners or complexing agents and/or nonaqueous solvents, such as, for example, ethanol, propylene glycol and/or glycerol.

Suitable astringent antiperspirant active ingredients are primarily salts of aluminum, zirconium or of zinc. Such suitable antihidrotic active ingredients are, for example, aluminum chloride, aluminum chlorohydrate, aluminum dichlorohydrate, aluminum sesquichlorohydrate and complex compounds thereof, e.g. with 1,2-propylene glycol, aluminum hydroxyallantoinate, aluminum chloride tartrate, aluminum zirconium trichlorohydrate, aluminum zirconium tetrachlorohydrate, aluminum zirconium pentachlorohydrate and complex compounds thereof, e.g. with amino acids, such as glycine. In addition, customary oil-soluble and water-soluble auxiliaries may be present in antiperspirants in relatively small amounts. such oil-soluble auxiliaries may, for example, be:

anti-inflammatory, skin-protective or perfumed essential oils, synthetic skin-protective active ingredients and/or oil-soluble perfume oils.

Customary water-soluble additives are, for example, preservatives, water-soluble fragrances, pH regulators, e.g. buffer mixtures, water-soluble thickeners, e.g. water-soluble natural or synthetic polymers, such as, for example, xanthan gum, hydroxyethylcellulose, polyvinylpyrrolidone or high molecular weight polyethylene oxides.

Antidandruff agents which may be used are Octopirox® (1-hydroxy-4-methyl-6-(2,4,4-trimethylpentyl)-2-(1H)-pyridone monoethanolamine salt), Baypival, piroctone olamine, ketoconazole (4-acetyl-1-{4-[2-(2,4-dichlorophenyl)-2-(1H-imidazol-1-ylmethyl)-1,3-dioxolan-4-yl-methoxyphenyl}piperazine, selenium disulfide, colloidal sulfur, gulfur polyethylene glycol sorbitan monoleate, sulfur ricinol polyethoxylate, sulfur tar distillate, salicylic acid (or in combination with hexachlorophene), undecylenic acid monoethanolamidesulfosuccinate Na salt, Lamepon® UD (protein undecylenic acid condensate), zinc pyrithione, aluminum pyrithione and magnesium pyrithione/dipyrithione magnesium sulfate.

Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof, and similar compounds.

The swelling agents for aqueous phases may be montmorillonites, clay mineral substances, Pemulen, and alkyl-modified Carbopol grades (Goodrich). Other suitable polymers and swelling agents are given in the review by R. Lochhead in Cosm. Toil. 108, 95 (1993).

The term "UV light protection factors" means, for example, organic substances (light protection filters) which are liquid or crystalline at room temperature and which are able to absorb ultraviolet rays and give off the absorbed energy again in the form of longer-wavelength radiation, e.g. heat. UVB filters can be oil-soluble or water-soluble. Examples of oil-soluble substances are:

3-benzylidenecamphor or 3-benzylidenenorcamphor and derivatives thereof, e.g. 3-(4-methylbenzylidene) camphor, as described in EP 0693471 B1;

4-aminobenzoic acid derivatives, preferably 2-ethylhexyl 4- (dimethylamino)benzoate, 2-octyl 4-(dimethylamino)benzoate and amyl 4-(dimethylamino)benzoate;

esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylene);

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably di-2-ethyl-hexyl 4-methoxybenzalmalonate;

triazine derivatives, such as, for example, 2,4,6-trianilino (p-carbo-2'-ethyl-1'-hexyloxy)-1,3,5-triazine and octyltriazone, as described in EP 0818450 A1 or dioctylbutamidotriazone (Uvasorb® HEB);

propane-1,3-diones, such as, for example, 1-(4-tert-butylphenyl)-3-(4'-methoxyphenyl)propane-1,3-dione;

ketotricyclo(5.2.1.0)decane derivatives, as described in EP 0694521 B1.

Suitable water-soluble substances are:

2-phenylbenzimidazole-5-sulfonic acid and the alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and its salts;

sulfonic acid derivatives of 3-benzylidenecamphor, such as, for example, 4-(2-oxo-3-bornylidenemethyl) benzenesulfonic acid and 2-methyl-S-(2-oxo-3-bornylidene) sulfonic acid and salts thereof.

Suitable typical UV-A filters are, in particular, derivatives of benzoylmethane, such as, for example, 1-(4'-tert-butylphenyl)-3-(4'-methoxyphenyl)propane-1,3-dione, 4-tert-butyl-4'-methoxydibenzoylmethane (Parsol 1789), 1-phenyl-3-(4'-isopropylphenyl)propane-1,3-dione, and enamine compounds, as described in DE 19712033 A1 (BASF). The UV-A and UV-B filters can of course also be used in mixtures. As well as said soluble substances, insoluble light protection pigments, namely finely dispersed metal oxides or salts, are also suitable for this purpose. Examples of suitable metal oxides are, in particular, zinc oxide and titanium oxide and also oxides of iron, zirconium, silicon, manganese, aluminum and cerium, and mixtures thereof. Salts which may be used are silicates (talc), barium sulfate or zinc atearate. The oxides and salts are used in the form of the pigments for skincare and skin-protective emulsions and decorative cosmetics. The particles here should have an average diameter of less than 100 nm, preferably between 5 and 50 nm and in particular between 15 and 30 nm. They can have a spherical shape, but it is also possible to use particles which have an ellipsoidal shape or a shape deviating in some other way from the spherical form. The pigments can also be surface-treated, i.e. hydrophilicized or hydrophobicized. Typical examples are coated titanium dioxides, such as, for example, titanium dioxide T 805 (Degussa) or Eusolex® T2000 (Merck). Suitable hydrophobic coating agents are here primarily silicones and, specifically in this case, trialkoxyoctylsilanes or simethicones. In sunscreens, preference is given to using so-called micro- or nanopigments. Preference is given to using micronized zinc oxide. Further suitable UV light protection filters are given in the review by P. Finkel in SÖFW-Journal 122, 543 (1996).

As well as the two abovementioned groups of primary light protection substances, it is also possible to uset secondary light protection agents of the antioxidant type; these interrupt the photochemical reaction chain which is triggered when UW radiation penetrates the skin. Typical examples thereof are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivativeg thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol to μmol/kg), and also (metal) chelating agents (e.g. α-hydroxy fatty acids, palmitic acid, phytic acid, lactoferrin), a-hydroxy acids (e.g. citric acid, lactic acid, malic acid), humic acid, bile acid, bile extracts, bilirubin, biliverdin, EDTA, EGTA and derivatives thereof, unsaturated fatty acid and derivatives thereof (e.g. γ-linolenic acid, linoleic acid, oleic acid)₁ folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of gum benzoin, rutic acid and derivatives thereof, α-glycosylrutin, ferulic acid, furfurylideneglucitol, carnosine, butylhydroxytoluene, butylhydroxyanisole, nordihydroguaiac acid, nordihydroguaiaretic acid, trihydroxybutyrophenone, uric acid and derivatives thereof, mannose and derivatives thereof, superoxide dismutase, zinc and derivatives thereof (e.g. ZnO, $ZnSO_4$) selenium and derivatiVes thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention.

To improve the flow behavior, it is furthermore possible to use hydrotropic agents, such as, for example, ethanol, isopropyl alcohol or polyols. Polyols which are suitable here preferably have 2 to 15 carbon atoms and at least two hydroxyl groups. The polyols can also contain further functional groups, in particular amino groups, or can be modified with nitrogen. Typical examples are glycerol;

alkylene glycols, such as, for example, ethylene glycol, diethylene glycol, propylene glycol, butylene glycol, hexylene glycol, and polyethylene glycols having an average molecular weight of from 100 to 1000 daltons;

technical-grade oligoglycerol mixtures having a degree of self-condensation of from 1.5 to 10, such as, for example, technical-grade diglycerol mixtures having a diglycerol content of from 40 to 50% by weight;

methylol compounds, such as, in particular, trimethylolethane, trimethylolpropane, trimethylolbutane, pentaerythritol and dipentaerythritol;

lower alkyl glucosides, in particular those having 1 to 8 carbon atoms in the alkyl radical, such as, for example, methyl and butyl glucoside;

sugar alcohols having 5 to 12 carbon atoms, such as, for example, sorbitol or mannitol;

sugars having 5 to 12 carbon atoms, such as, for example, glucose or sucrose;

aminosugars, such as, for example, glucamine;

dialcoholamines, such as diethanolamine or 2-amino-1,3-propanediol.

Suitable preservatives are, for example, phenoxyethanol, formaldehyde solution, parabens, pentanediol or sorbic acid, and the other classes of substance listed in Annex 6, Part A and B of the Cosmetics Directive. Suitable insect repellants are N,N-diethyl-m-toluamide, 1,2-pentanediol -or ethyl butylacatylamino-propionate, and a suitable self-tanning agent is dihydroxyacetone. Suitable tyrosine inhibitors, which prevent the formation of melanin and are used in depigmentation agents, are, for example, arbutin, kojic acid, coumaric acid and ascorbic acid (vitamin C).

Perfume oils which may be mentioned are mixtures of natural and synthetic fragrances. Natural fragrances are extracts from flowers (lily, lavender, rose, jasmine, neroli, ylang-ylang), stems and leaves (geranium, patchouli, petitgrain), fruits (aniseed, coriander, cumin, juniper), fruit peels (bergamot, lemon, orange), roots (mace, angelica, celery, cardamom, costus, iris, calmus), woods (pine wood, sandalwood, guaiac wood, cedarwood, rosewood), herbs and grasses (tarragon, lemon grass, sage, thyme), needles and branches (spruce, fir, pine, dwarf-pine), resins and balsams (galbanum, elemi, benzoin, myrrh, olibanum, opoponax). Also suitable are animal raw materials, such as, for example, civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bourgeonal, and the ketones include, for example, the ionones, α-isomethylionone and methyl cedryl ketone, the alcohols include anethol, citronellol, eugenol, isoeugenol, geraniol, linalool, phenylethyl alcohol and terpineol, and the hydrocarbons include predominantly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden blossom oil, juniper berry oil, vetiver oil, olibanum oil, galbanum oil, labolanum oil and lavandin oil, preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-Super, Fixolide NP, evernyl, iraldein gamma, phenylacetic acid, geranyl acetate, benzyl acetate, rose oxide, romilat, irotyl and floramat alone or in mixtures.

Dyes which can be used are the substances which are approved and suitable for cosmetic purposes, as are listed, for example, in the publication "Kosmetiuche Färbemittel" [Cosmetics Colorants] from the Farbstoff-komnission der Deutschen Forschungsgemeinschaft [Dyes Commission of the German Research Council], Verlag Chemie, Weinheim, 1984, pp. 81–106. These dyes are normally used in concentrations of from 0.001 to 0.1% by weight, based on the total mixture.

The total amount of auxiliaries and additives can be 1 to 50% by weight, preferably 5 to 40% by weight, based on the compositions. The compositions can be prepared by customary cold or hot processes; preference is given to using the phase-inversion temperature method.

EXAMPLES

Preparation of Lanette® E liquid.

In a continuously operating falling-film reactor (length 120 cm, cross section 1 cm, starting material throughput 600 g/h) with jacket cooling and sidestream $SO_3$ gassing, 5.0 mol of different mixtures of cetylstearyl alcohol (ROH) and $C_{12/14}$-coconut fatty alcohol +2 EO (ROH+2) were reacted with 4.9 mol of gaseous sulfur trioxide at 35° C. During the process, the acidic reaction mixture was introduced continuously into 10% strength by weight sodium hydroxide solution and neutralized. The aqueous surfactant solution was adjusted to pH =7.8. The anionic surfactant content (WAS) and the nonsulfonated fractions (US) were determined in accordance with the DGF standard methods, Stuttgart 1950–1984, H-III-10 and G-II-6b. The Klett color number was determined after bleaching for 30 minutes with 1% by weight of a 35% strength by weight aqueous hydrogen peroxide solution. The measurement was carried out at a concentration of 5% by weight of anionic surfactant, pH=7 and using a 1 cm round cell, and a blue filter (400 to 465 nm). The results are given in Table 1:

TABLE 1

Preparation of Lanette ® liquid

| Composition | 1 | 2 | 4 | 5 | 6 |
|---|---|---|---|---|---|
| ROH+2:ROH weight ratio | 90:10 | 85:15 | 80:20 | 75:25 | 0:30 |
| WAS [% by weight] | 64.4 | 67.3 | 65.8 | 65.7 | 64.7 |
| US [% by weight] | 5.2 | 5.1 | 5.0 | 5.2 | 5.3 |
| Na$_2$SO$_4$ [% by weight] | 1.2 | 1.3 | 1.1 | 1.2 | 1.2 |
| Water [% by weight] | 29.2 | 26.3 | 28.1 | 27.9 | 26.8 |
| Color number [Klett] | 40 | 42 | 42 | 40 | 41 |

Table 2 below gives a number of formulation examples.

TABLE 2

Cosmetic preparations (water, preservative ad 100% by weight)

| Composition (INCI) | 1 | 2 | 3 | 4 | 5 | 6 | 7 | 8 | 9 | 10 |
|---|---|---|---|---|---|---|---|---|---|---|
| Lanette ® E liquid | 20.0 | 20.0 | 12.4 | 20.0 | 25.0 | 11.0 | 5.0 | 5.0 | 11.0 | 23.0 |
| Sodium laureth sulfate and sodium lauryl sulfate | | | | | | | | | | |
| Texapon ® SB 3 | — | — | — | — | — | 7.0 | — | — | — | — |
| Disodium laureth sulfosuccinate | | | | | | | | | | |
| Plantacare ® 818 | 5.0 | 5.0 | 4.0 | — | — | — | — | — | 6.0 | 4.0 |
| Coco glucosides | | | | | | | | | | |
| Plantacare ® 2000 | — | — | — | — | 5.0 | 4.0 | 11.0 | 10.0 | — | — |
| Decyl glucoside | | | | | | | | | | |
| Plantacare ® PS 10 | — | — | — | 20.0 | — | — | — | — | — | — |
| Sodium laureth sulfate (and) coco glucosides | | | | | | | | | | |
| Dehyton ® PK 45 | 20.0 | 20.0 | — | — | 8.0 | — | — | — | — | 7.0 |
| Cocamidopropyl betaine | | | | | | | | | | |
| Eumulgin ® B1 | — | — | — | — | 1.0 | — | — | — | — | — |
| Ceteareth-12 | | | | | | | | | | |
| Eumulgin ® B2 | — | — | — | 1.0 | — | — | — | — | — | — |
| Ceteareth-20 | | | | | | | | | | |
| Lameform ® TGI | — | — | — | 4.0 | — | — | — | — | — | — |
| Polyglyceryl-3 isostearate | | | | | | | | | | |
| Dehymuls ® PGPH | — | — | 1.0 | — | — | — | — | — | — | — |
| Polyglyceryl-2 dipolyhydroxystearate | | | | | | | | | | |
| Monomuls ® 90-L 12 | — | — | — | — | — | — | — | — | 1.0 | 1.0 |
| Glyceryl laurate | | | | | | | | | | |
| Cetiol ® HE | — | 0.2 | — | — | — | — | — | — | — | — |
| PEG-7 glyceryl cocoate | | | | | | | | | | |
| Eutanol ® G | — | — | — | 3.0 | — | — | — | — | — | — |
| Octyldodecanol | | | | | | | | | | |
| Nutrilan ® Keratin W | — | — | — | — | — | — | — | — | 2.0 | 2.0 |
| Hydrolyzed keratin | | | | | | | | | | |
| Nutrilan ® I | 1.0 | — | — | — | — | 2.0 | — | 2.0 | — | — |
| Hydrolyzed collagen | | | | | | | | | | |
| Lamesoft ® LMG | — | — | — | — | — | — | — | — | 1.0 | — |
| Glyceryl laurate (and) potassium cocoyl hydrolyzed collagen | | | | | | | | | | |
| Lamesoft ® 156 | — | — | — | — | — | — | — | — | — | 5.0 |
| Hydrogenated tallow glyceride (and) potassium cocoyl hydrolyzed collagen | | | | | | | | | | |
| Gluadin ® WK | 1.0 | 1.5 | 4.0 | 1.0 | 3.0 | 1.0 | 2.0 | 2.0 | 2.0 | — |
| Sodium cocoyl hydrolyzed wheat protein | | | | | | | | | | |
| Euperlan ® PK 3000 AM | 5.0 | 3.0 | 4.0 | — | — | — | — | 3.0 | 3.0 | — |
| Glycol distearate (and) laureth-4 (and) cocamidopropyl betaine | | | | | | | | | | |
| Panthenol | — | — | 1.0 | — | — | — | — | — | — | — |
| Arlyon ® F | 2.6 | 1.6 | — | 1.0 | 1.5 | — | — | — | — | — |
| Laureth-2 | | | | | | | | | | |
| Highcareen ® GS | 1.0 | 1.0 | 1.0 | 1.0 | 1.0 | 1.0 | 1.0 | 1.0 | 1.0 | 1.0 |
| Betaglucan | | | | | | | | | | |
| Hydagen ® CMF | 1.0 | 1.0 | 1.0 | 1.0 | 1.0 | 1.0 | 1.0 | 1.0 | 1.0 | 1.0 |
| Chitosan | | | | | | | | | | |
| Sodium Chloride | — | — | — | — | 1.6 | 2.0 | 2.2 | — | 3.0 | |
| Glycerol (86% strength by weight) | — | 5.0 | — | — | — | — | — | 1.0 | 3.0 | — |

(1–4) "two-in-one" shower preparation, (5–10) shampoo

What is claimed is:

1. A high-concentrate flowable liquid anionic surfactant composition comprising:

(a) from 60 to 90% by weight of an alkyl ether sulfate corresponding to formula I:

$$R^1O(CH_2CH_2O)_nSO_3X \qquad (I)$$

wherein $R^1$ is a linear or branched alkyl radical having from 12 to 22 carbon atoms, n is a number having a value of from 1 to 10, and X is an alkali metal, alkaline earth metal, ammonium, alkylammonium, alkanolammonium or glucammonium; and (b) from 10 to 40% by weight of an alkyl sulfate corresponding to formula II:

$$R^2OSO_3X \qquad (II)$$

wherein $R^2$ is a linear or branched alkyl radical having from 12 to 22 carbon atoms, and X is an alkali metal, alkaline earth metal, ammonium, alkylammonium, alkanolammonium or glucammonium, all weights being based on the total weight of the composition, and wherein the composition has a solids content of from 50 to 80% by weight.

2. The composition of claim 1 wherein the composition has a solids content of from 65 to 75% by weight.

3. The composition of claim 1 wherein the alkyl ether sulfate is present in the composition in an amount of from 75 to 85% by weight, based on the weight of the composition.

4. The composition of claim 1 wherein in formula (I), $R^1$ is an alkyl radical having from 12 to 18 carbon atoms, and n is a number from 2 to 5.

5. The composition of claim 1 wherein the alkyl sulfate is present in the composition in an amount of from 15 to 25% by weight, based on the weight of the composition.

6. The composition of claim 1 wherein in formula (II), $R^2$ is an alkyl radical having from 16 to 18 carbon atoms.

7. The composition of claim 1 wherein the composition has a Brookfield viscosity of less than 50,000 mPas.

8. A personal care composition comprising from 0.1 to 50% by weight, based on the weight of the personal care composition, of the surfactant composition of claim 1.

9. A process for making a high-concentration, flowable liquid anionic surfactant composition comprising:

(a) providing from 60 to 90% by weight of an alcohol polyglycol ether corresponding to formula III:

$$R^3O(CH_2CH_2O)_nH \qquad (III)$$

wherein $R^3$ is a linear or branched alkyl radical having from 12 to 22 carbon atoms, n is a number having a value of from 1 to 10;

(b) providing from 10 to 40% by weight of an alcohol corresponding to formula IV:

$$R^4OH \qquad (IV)$$

wherein $R^4$ is a linear or branched alkyl radical having from 12 to 22 carbon atoms;

(c) mixing (a) and (b) to form a primary mixture;

(d) sulfating the primary mixture;

(e) neutralizing the primary mixture; and (f) adjusting the solids content of the primary mixture to from 50 to 80% by weight, to form the high-concentration, flowable liquid anionic surfactant composition.

10. The process of claim 9 wherein the solids content of the composition is adjusted to from 65 to 75% by weight.

11. The process of claim 9 wherein the alcohol polyglycol ether is provided in an amount of from 75 to 85% by weight, based on the weight of the composition.

12. The process of claim 9 wherein in formula (I), $R^3$ is an alkyl radical having from 12 to 18 carbon atoms, and n is a number from 2 to 5.

13. The process of claim 9 wherein the alcohol is provided in an amount of from 15 to 25% by weight, based on the weight of the composition.

14. The process of claim 9 wherein in formula (II), $R^4$ is an alkyl radical having from 16 to 18 carbon atoms.

15. The process of claim 9 wherein the composition has a Brookfield viscosity of less than 50,000 mPas.

16. The process of claim 9 wherein the primary mixture is sulfated using gaseous sulfur trioxide or chlorosulfonic acid.

17. The process of claim 9 further comprising bleaching the primary mixture, after step (e).

18. The process of claim 17 wherein the primary mixture is bleached using hydrogen peroxide or sodium hypochlorite.

* * * * *